United States Patent [19]

Hamada et al.

[11] Patent Number: 4,824,549
[45] Date of Patent: Apr. 25, 1989

[54] EXHAUST GAS SENSOR FOR DETERMINING A/F RATIO

[75] Inventors: Yasuhiko Hamada; Tsunenori Yoshimura, both of Nagoya, Japan

[73] Assignee: NGK Insulators, Ltd., Nagoya, Japan

[21] Appl. No.: 137,349

[22] Filed: Dec. 23, 1987

[30] Foreign Application Priority Data

Dec. 27, 1986 [JP] Japan .................. 61-311196
Mar. 2, 1987 [JP] Japan .................. 62-46998

[51] Int. Cl.⁴ .................................. G01N 27/58
[52] U.S. Cl. ............................ 204/410; 204/412
[58] Field of Search ............... 204/410, 412, 425, 1 S

[56] References Cited

U.S. PATENT DOCUMENTS

4,285,790 8/1981 Isenberg .................. 204/410
4,728,411 3/1988 Mase et al. .............. 204/425

Primary Examiner—G. L. Kaplan
Attorney, Agent, or Firm—Parkhurst, Oliff & Berridge

[57] ABSTRACT

An oxygen sensor for detecting a measurement gas such as exhaust gases existing in an external space, which has a sensing element having a gas-diffusion space which communicates with the external space. The gas-diffusion space has a predetermined resistance to diffusion of the measurement gas therethrough, and includes a first portion to which the measurement gas diffuses along a first diffusion path, and a second portion to which the measurement gas diffuses through the first portion along a second diffusion path which has a larger length than the first diffusion path. The sensing element has a first sensing unit for producing a first output representative of an oxygen concentration of an atmosphere in the first portion of the gas-diffusion space, a first pumping unit responsive to the first output, for controlling the oxygen concentration of the atmosphere in the first portion of the gas-diffusion space, a second sensing unit for producing a second ouput representative of an oxygen concentration of an atmosphere in the second portion of the gas-diffusion space, and a second pumping unit responsive to the second output, for for controlling the oxygen concentration of the atmosphere in the second portion of the gas-diffusion space.

21 Claims, 6 Drawing Sheets

EXHAUST GAS SENSOR FOR DETERMINING A/F RATIO

BACKGROUND OF THE INVENTION

1. Field of the Invention

The present invention relates in general to an oxygen sensing apparatus, in particular, an apparatus adapted to sense exhaust gases such as those emitted by internal combustion engines of a motor vehicle or various industrial furnaces, and more specifically to such an exhaust-gas sensing apparatus used for a combustion control system for the internal combustion engines and industrial furnaces, to determine an air/fuel (A/F) ratio of an air-fuel mixture supplied to the engines and furnaces. In particular, the invention relates to such an A/F-ratio sensor which has a function of compensating for its chronological changes in the operating characteristics and deterioration in the durability.

2. Discussion of the Prior Art

As an oxygen sensor for determining an oxygen concentration of combustion exhaust gases emitted for example by automotive internal combustion engines, there is known a sensor which utilizes a zirconia ceramic or other oxygen-ion conductive solid electrolyte material and which is operated to determine the oxygen concentration according to the principle of an oxygen concentration cell. For operating an internal combustion engine, it is required to accurately control an air/fuel (A/F) ratio of an air-fuel mixture supplied to the engine, such that the actual air/fuel ratio coincides with a desired value. Generally, this air/fuel ratio is determined by measuring the concentration of oxygen in the exhaust gases, which is varied as a function of the air/fuel ratio of the air-fuel mixture supplied to the engine. A signal representative of the determined air/fuel ratio is fed to a fuel supply control system of the engine, in order to determine an amount of supply of the fuel, i.e., to control the actual air/fuel ratio so as to coincide with the desired value.

An example of such an oxygen sensor (oxygen-concentration detector) used as an A/F ratio sensor is proposed in U.S. Pat. No. 4,568,443. In the oxygen sensor proposed in this publication, a sensing element of the sensor is formed with an internal gas-diffusion space which communicates with an external measurement-gas space in which there exist exhaust gases (hereinafter referred to as "measurement gas" when appropriate) to be measured. The sensing element has detecting means for detecting the oxygen concentration of the atmosphere within the internal gas-diffusion space, which consists of the measurement gas which is introduced under a predetermined diffusion resistance. The detecting means produces an output indicative of the oxygen concentration of the atmosphere within the gas-diffusion space. The sensing element also has oxygen pumping means which is operated with a pump current based on the output of the detecting means, so that the oxygen concentration within the diffusion-gas space is maintained at a predetermined level. The pump current applied to the oxygen pumping means is measured as a parameter which represents the oxygen concentration of the measurement gas, i.e., exhaust gases which are produced as a result of combustion of an air-fuel mixture. Namely, the pump current represents the air/fuel ratio of the air-fuel mixture.

Figure 2:
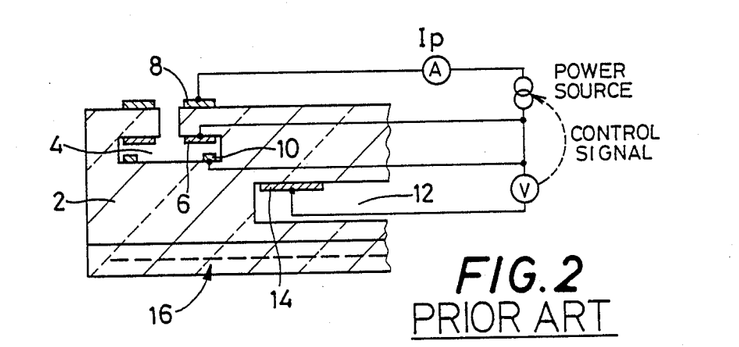
FIG. 2 is a view corresponding to that of FIG. 1, showing an example of a known A/F-ratio sensor.

Described more specifically referring to FIG. 2, the sensing element of the A/F-ratio sensor of the type discussed above includes a first electrochemical cell in the form of an oxygen pumping cell which comprises a solid electrolyte body 2, an inner pumping electrode 6 which is exposed to an internal flat gas-diffusion space 4 communicating with an external measurement-gas space, and an outer pumping electrode 8 which is substantially exposed to the external space. The sensing element further includes a second electrochemical cell (oxygen concentration cell) in the form of an oxygen sensing cell which comprises the solid electrolyte body 2, a measuring electrode 10 which is exposed to the internal flat gas-diffusion space 4, and a reference electrode 14 which is exposed to an air passage 12 communicating with the ambient air. The sensing element incorporates a heater 16 adapted to keep these two oxygen pumping and sensing cells at suitable operating temperatures. The oxygen sensor having this sensing element is capable of dealing with not only stoichiometric exhaust gases, but also lean-burned exahust gases and rich-burned exhaust gases. The stoichiometric exhaust gases are exhaust gases which are produced as a result of combustion of an air-fuel mixture whose A/F ratio is equal to or near the stochiometric value (A/F=14.6) or whose excess air factor ($\lambda$) is equal to or near "1". The lean-burned exhaust gases are exhaust gases produced by combustion of an air-fuel mixture whose A/F ratio (excess air factor) is larger than the stoichiometric value ($\lambda > 1$), while the rich-burned exhaust gases are exhaust gases emitted by combustion of an air-fuel mixture whose A/F ratio (excess air factor) is smaller than the stoichiometric value ($\lambda < 1$). Thus, the instant oxygen sensor is capable of determining the A/F ratios of the air-fuel mixtures which give these different types of exhaust gases.

In the A/F-ratio sensor of the type described above, the measurement gas is introduced from the external measurement-gas space into the internal gas-diffusion space 4 under the predetermined diffusion resistance, so that the introduced measurement gas contacts the measuring electrode 10 of the oxygen sensing cell. In the meantime, an electric current, so-called "pump current" (Ip) is applied between the inner and outer pumping electrodes 6, 8 disposed within and outside the gas-diffusion space 4, so that a well known oxygen pumping action is performed such that the oxygen concentration of the atmosphere adjacent to the measuring electrode 10 is maintained at a predetermined level, due to the reaction of the pumping electrodes 6, 8. According to this arrangement, the pump current (Ip) is varied with a change in the concentration of a desired measurement component (i.e., oxygen concentration) of the measurement gas (exhaust gases), that is, with a variation in the excess air factor ($\lambda$) or A/F ratio of the air-fuel mixture which gives the exhaust gases. Consequently, the measurement of the pump current (Ip) makes it possible to determine the excess air factor ($\lambda$) of an air-fuel mixture which is higher or lower than "1", or the A/F ratio of the same which is higher or lower than the stoichiometric level. In other words, the instant A/F-ratio sensor is capable of dealing with not only the lean-burned exhaust gases which are produced as a result of an air-rich air-fuel mixture and which has a higher oxygen partial pressure than the stoichiometric exhaust gases, but also the rich-burned exhaust gases which are produced as a result of a fuel-rich air-fuel mixture and which has a lower oxygen partial pressure than the stoichiometric exhaust gases. The rich-burned exhaust gases contain a large amount of unburned components.

Figure 3:
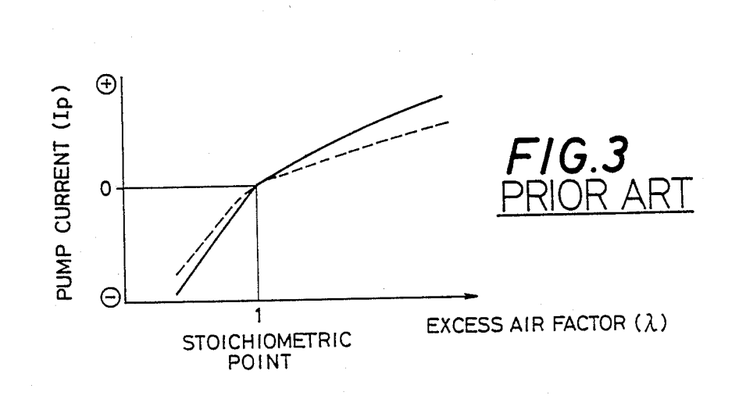
FIG. 3 is a graph illustrating a chronological change of the output characteristic (relationship between pump current Ip and excess air factor) of the known A/F-ratio sensor.

Thus, the A/F ratio of an air-fuel mixture can be determined by detecting a pump current (Ip) across the pair of pumping electrodes, which is varied with the oxygen concentration of the exhaust gases produced from the air-fuel mixture. The pump current (Ip) is expressed by the following equation:

Ip=A (Pe−Po)/R where,
Pe=oxygen partial pressure of the exhaust gases
Po=oxygen partial pressure of the atmosphere within the gas-diffusion space 4
R=resistance to diffusion of the exhaust gases from the external space into the gas-diffusion space 4
A=proportion constant Thus, the pump current (Ip) is influenced by the diffusion resistance (R) of the sensing element. The diffusion resistance (R) is changed during use of the A/F-ratio sensor, if the geometrical configuration of the diffusion path of the exhaust gases (measurement gas) is changed due to deposition of particles contained in the exhaust gases. Accordingly, the output of the A/F-ratio sensor in the form of the pump current (Ip) in relation to the excess air factor (A/F ratio) is changed from the state indicated in solid line in FIG. 3, to the state indicated in dashed line. Hence, the sensor suffers from a chronological change in its output characteristic, i.e., relationship between the pump current (Ip) and the A/F ratio.

SUMMARY OF THE INVENTION

It is therefore an object of the present invention to provide an apparatus for determining an air/fuel ratio of an air-fuel mixture by sensing exhaust gases produced from the air-fuel mixture, which apparatus is substantially free from the conventionally experienced chronological change in its output characteristic.

The above object may be achieved according to the principle of the present invention, which provides an oxygen sensor for detecting a measurement gas such as exhaust gases existing in an external space, which has a sensing element which includes means for defining a gas-diffusion space communicating with the external space. The gas-diffusion space has a predetermined resistance to diffusion of the measurement gas therethrough, and includes a first portion to which the measurement gas diffuses along a first diffusion path, and a second portion to which the measurement gas diffuses through the first portion along a second diffusion path which has a larger length than the first diffusion path. The sensing element further includes first oxygen sensing means, first oxygen pumping means, second oxygen sensing means and second oxygen pumping means. The first oxygen sensing means is adapted to produce a first output representative of an oxygen concentration of an atmosphere in the first portion of the gas-diffusion space. The first oxygen pumping means is responsive to the first output from the first oxygen sensing means, for effecting an oxygen pumping action for controlling the oxygen concentration of the atmosphere in the first portion of the gas-diffusion space. The second oxygen sensing means is adapted to produce a second output representative of an oxygen concentration of an atmosphere in the second portion of the gas-diffusion space. The second oxygen pumping means is responsive to the second output from the second oxygen sensing means, for effecting an oxygen pumping action for controlling the oxygen concentration of the atmosphere in the second portion of the gas-diffusion space.

According to one feature of the invention, the diffusion-gas space consists of a thin flat space which communicates with the external space directly, or through a gas-inlet aperture.

For example, the thin flat space may be a circular flat space having a thickness in a direction perpendicular to a major surface of the sensing element. The circular flat space has a central portion which communicates with the gas-inlet aperture. In this case, the first portion consists of an annular portion disposed adjacent to and radially outwardly of the central portion, while the second portion consists of an annular portion disposed radially outwardly of the first portion. Alternatively, the gas-diffusion space may be a generally elongate straight space. In this case, the first and second portions are spaced apart from each other along a length of the straight space. According to a further form of the above feature of the invention, the thin flat space consists of a generally spiral space having a thickness in a direction perpendicular to a major surface of the sensing element. The generally spiral space communicates at one of its opposite ends with the gas-inlet aperture. In this case, the first portion is disposed adjacent to the above-indicated one end portion, while the second portion consists of the other end portion.

According to another feature of the invention, each of the first and second oxygen sensing means and the first and second oxygen pumping means consists of an electrochemical cell which comprises a solid electrolyte body, and a pair of electrodes. The four electrochemical cells are incorporated in an integral structure of the sensing element. The solid electrolyte body of the electrochemical cells of the first and second sensing means and the first and second pumping means is preferably formed of an oxygen-ion conductive zirconia ceramic. The sensing element may further comprise a heater for maintaining the solid electrolyte body of each of the four electrochemical cells at a predetermined operating temperature.

In one form of the above feature of the invention, one of the pair of electrodes of the first oxygen sensing means, and one of the pair of electrodes of the second oxygen sensing means are disposed in the first and second portions of the gas-diffusion space, respectively, and the other electrode of the first oxygen sensing means and the other electrode of the second oxygen sensing means are constituted by a single common electrode which is disposed outside the gas-diffusion space. This single common electrode may be a reference electrode exposed to a reference atmosphere which has a predetermined oxygen partial pressure.

In another form of the above feature of the invention, one of the pair of electrodes of the first oxygen pumping means, and one of the pair of electrodes of the second oxygen pumping means are disposed in the first and second portions of the gas-diffusion space, respectively, and the other electrode of the first oxygen pumping means and the other electrode of the second oxygen pumping means are constituted by a single common electrode which is disposed outside the gas-diffusion space.

According to a further feature of the invention, the diffusion resistance of the gas-diffusion space is determined so that a first pump current which is applied to the first oxygen pumping means so as to maintain the oxygen concentration of the atmosphere in the first portion at a predetermined value is at least two times as large as a second pump current which is applied to the second oxygen pumping means so as to maintain the oxygen concentration of the atmosphere in the second portion at the predetermined value. This arrangement improves the sensitivity of the sensor, and permits compensation of the sensor output for a change in the diffusion resistance of the gas-diffusion space during use of the sensor.

According to a still further feature of the invention, the sensing element further comprises additional diffusion-resistance means which is disposed in a third portion of the gas-diffusion space. The third portion is disposed between the first and second portions, or includes the second portion. This additional diffusion-resistance means has a predetermined resistance to diffusion of the measurement gas therethrough, which is greater than the resistance of the diffusion-resistance means.

In one form of the above feature of the invention, the additional diffusion-resistance means consists of a porous body disposed in the third portion of the gas-diffusion space.

Where the gas-diffusion space communicates with the external space through a suitable aperture, the sensing element may further comprise a porous body which fills the aperture. This porous body may be provided in addition to the above-indicated porous body disposed in the gas-diffusion space.

In accordance with another feature of the invention, the sensing element further comprises partition means disposed between the first and second portions of the gas-diffusion space, so as to prevent a linear diffusion of the measurement gas from the first portion to the second portion, thereby providing a diffusion path which is longer than a length of the linear diffusion.

The porous body or other additional diffusion-resistance means or the partition means indicated above is effective to establish a distribution of diffusion resistance within the sensing element, so that the pump current applied to the first oxygen pumping means is at least two times as high as the pump current applied to the second oxygen pumping means.

In the oxygen sensor of the present invention constructed as described above, a first pump current is applied to the first oxygen pumping means so that the oxygen concentration of the atmosphere in the first portion of the gas-diffusion space is maintained at a predetermined value. At the same time, a second pump current is applied to the second oxygen pumping means so that the oxygen concentration of the atmosphere in the second portion of the gas-diffusion space is maintained at the above-indicated predetermined value. Based on a ratio of the first pump current to the second pump current, it is possible to compensate for the sensor output for a chronological change in the diffusion resistance of the diffusion path between the external space and the gas-diffusion space within the sensing element, during a long period of service of the sensor. Where the measurement gas is exhaust gases produced as a result of combustion of an air-fuel mixture, the sensor output represents an air/fuel ratio of the air-fuel mixture.

The principle on which the sensor output is compensated according to the present invention will be described below in detail. Suppose an oxygen sensor is used as an A/F-ratio sensor for determining an air-fuel ratio of an air-fuel mixture, by detecting the oxygen concentration of exhaust gases which are produced by combustion of the air-fuel mixture, and suppose the sensing element of the A/F-ratio sensor has oxygen sensing means and oxygen pumping means, so that the atmosphere within the gas-diffusion space within the sensing element is controlled to a desired value by the oxygen pumping means based on an output of the oxygen sensing means which represents the actual oxygen concentration within the gas-diffusion space. In this oxygen sensor, a pump current Ip which flows through the oxygen pumping means is expressed by the following equation (1):

$$Ip = 4e\sigma_0 (P_{O_2}ehx - P_{O_2}v) \quad (1)$$

where, $\sigma_0$: resistance to diffusion of exhaust gases through the gas-diffusion space $P_{O_2}ehx$: oxygen concentration of exhaust gases in external space $P_{O_2}v$: oxygen concentration of atmosphere within gas-diffusion space e: electric charge The diffusion resistance $\sigma^0$ is expressed by the following equation (2):

$$\sigma^0 = DA/kTl \quad (2)$$

where,

D: diffusion constant of oxygen

A: cross sectional area of gas-diffusion space k: Boltzmann's constant

T: absolute temperature l: length of diffusion through gas-diffusion space

Figure 4:
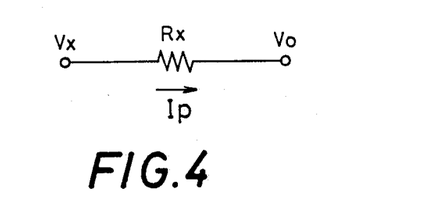
FIG. 4 is an electric circuit illustrating a detecting method of an A/F-ratio sensor.

The principle of measurement of the A/F-ratio sensor indicated above may be represented by an electric circuit (provided the absolute temperature T is constant) as exemplified in FIG. 4. The current Ip which flows through an electrical resistance Rx can be expressed by the following equation (3):

$$Ip = Rx^{-1}(Vx - Vo) \quad (3)$$

where,

Vx: potential at a point upstream of the resistor

Vo: potential at a point downstream of the resistor

In a common A/F-ration sensor, the atmosphere in a portion of the gas-diffusion space, whose oxygen concentration is detected, is controlled to be the stoichiometric atmosphere which is identical with the exhaust gases which are produced as a result of combustion of a stochiometric air-fuel mixture whose excess air factor ($\lambda$) is "1" (i.e., hose A/F ratio is 14.6). Namely, the oxygen concentration $P_{O_2}v$ of the atmosphere within the gas-diffusion space is zero, whereby Vo in the equation (3) is zero. Therefore, the equation (3) is converted into the following equation (4):

$$Ip = Vx/Rx \quad (4)$$

It follows from the equation (4) that the current Ip (pump curent) must be compensated for a variation in the electrical resistance Rx (equivalent to the diffusion resistance of the gas-diffusion space). That is, the variation in the resistance Rx due to deterioration of the sensor during use must be detected to accomplish the compensation of the sensor output Ip. The variation in the resistance Rx can be detected based on a ratio of a first output of the sensor when the diffusion resistance is at a first value, and a second output of the sensor when the diffusion resistance is at a second value.

Figure 5:
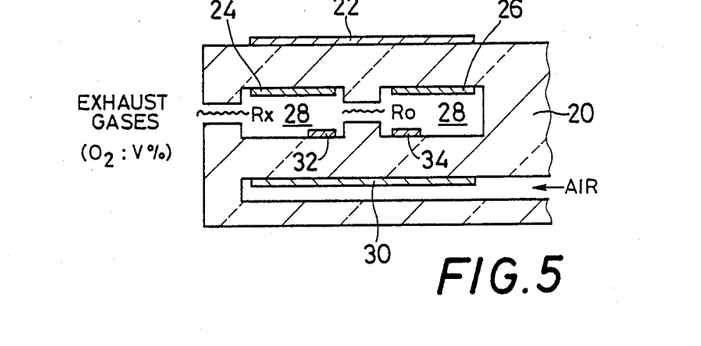
FIG. 5 is an elevational view in cross section showing the principle of the present invention.

Described more particularly referring to FIG. 5, a first oxygen pumping cell is constituted by a solid electrolyte body 20 and a pair of electrodes 22, 24, while a second oxygen pumping cell is constituted by the solid electrolyte body 20 and a pair of electrodes 22, 26. Further, a first oxygen sensing cell is constituted by the solid electrolyte body 20 and a pair of electrodes 30, 32, while a second oxygen sensing cell is constituted by the solid electrolyte body 20 and a pair of electrodes 30, 34. The electrodes 24, 26, 32, 34 are exposed to a gas-diffusion space 28. The first and second oxygen sensing cells are adapted to detect the oxygen concentrations of the atmospheres in the space 28 which correspond to the inner pumping electrodes 24, 26 of the first and second oxygen pumping cells, respectively. The measurement gas (exhaust gases) diffuses first into a first portion of the gas-diffusion space 28 in which the electrodes 24, 32 of the first pumping and sensing cells are exposed. The introduced measurement gas then diffuses into a second portion of the space 28 in which the electrodes 26, 34 are disposed. The pump current Ip1 when only the first pumping cell is operated is expressed by the following equation (5):

$$Ip1 = (V - Vo)/Rx \qquad (5)$$

where,

Rx: resistance to diffusion of the measurement gas into the first portion of the space 28

Ro: resistance to diffusion of the measurement gas into the second portion of the space 28

V (%): oxygen concentration of the measurement gas (exhaust gases) in the external space Vo (%): oxygen concentration of the atmosphere in the first or second portion of the space 28, which is established by the operation of the first or second pumping cell Where Vo is zero, therefore, $$Ip1 = V/Rx \qquad (5')$$

The pump current Ip2 when only the second pumping cell is operated is expressed by the following equation (6):

$$Ip2 = (V - Vo)/(Rx + Ro) \qquad (6)$$

Where Vo is zero, therefore, $$Ip2 = V/(Rx + Ro) \qquad (6')$$

Suppose "A" represents the initial ratio of the pump current Ip1 to the pump current Ip2 while the sensing element is new (while the diffusion resistances Rx and Ro of the gas-diffusion space 28 are substantially equal to the nominal values), the following equation (7) is obtained from the above equations (5') and (6'):

$$A = Ip1/Ip2 = (Rx + Ro)/Rx = 1 + Ro/Rx$$

Thus, $$Ro/Rx = A - 1 \qquad (7)$$

Suppose the diffusion resistance Rx corresponding to the first or outer portion of the space 28 is changed during use of the sensing element while the diffusion resistance Ro corresponding to the second or inner portion of the space 28 is kept constant, the following equations (8) and (9) are obtained in the same manner as the above equations (5') and (6'):

$$Ip1' = v/Rx' \qquad (8)$$

$$Ip2' = v/(Rx' + Ro) \qquad (9)$$

where, v: oxygen concentration of the measurement gas (exhaust gases) measured by the sensor which has served a given period of time Ip1': pump current of the first pumping cell Ip2': pump current of the second pumping cell Rx': diffusion resistance corresponding to the first portion of the space 28, after the given period of service of the sensor Suppose "B" represents the ratio of the pump current Ip1' to the pump current Ip2', the following equation (10) is be obtained from the above equations (8) and (9):

$$B = Ip1'/Ip2' = (Ro + Rx')/Rx' = 1 + Ro/Rx'$$

Thus, $$Ro/Rx' = B - 1 \qquad (10)$$

Accordingly, compensation factors C and D for the first and second oxygen pumping cells are expressed by the following equations (11) and (12), respectively, which are obtained from the above equations (5) through (10):

$$C = Ip1/Ip1' = (V/Rx)/(V/Rx') = (Rx'/Ro)/(Rx/Ro) = (A-1)/(B-1) \qquad (11)$$

$$D = Ip2/Ip2' = (V/Rx + Ro)/(V/Rx' + Ro) = (Rx'/Ro + 1)/(Rx/Ro + 1) = A/B \cdot (A-1)/(B-1) \qquad (12)$$

By obtaining the pump currents Ip1, Ip1' and Ip2 and Ip2' of the first and second pumping cells, the compensation factors C and D for the first and second pumping cells can be obtained based on the ratios A and B.

It will be understood from the foregoing explanation that the instant oxygen sensor which has the first and second oxygen sensing means and the first and second oxygen pumping means according to the principle of the present invention permits easy compensation of its output for a variation in the diffusion resistance of the gas-diffusion space during its use, so that the sensor output is adjusted so as to correctly represent the actual oxygen concentration of the measurement gas, as in the initial period of use. Therefore, where the instant oxygen sensor is used as an A/F-ratio sensor for exhaust gases emitted from an internal combustion engine, the sensor can serve for a prolonged period of time, for determining and controlling the air/fuel ratio of an air-fuel mixture supplied to the engine, even after the diffusion resistance of the gas-diffusion space within the sensing element is changed due to chronological deterioration.

BRIEF DESCRIPTION OF THE DRAWINGS

The above and other objects, features and advantages of the present invention will be better understood by reading the following detailed description of presently preferred embodiments of the invention, when considered in connection with the accompanying drawings, in which.

DETAILED DESCRIPTION OF THE PREFERRED EMBODIMENTS

Figure 1:
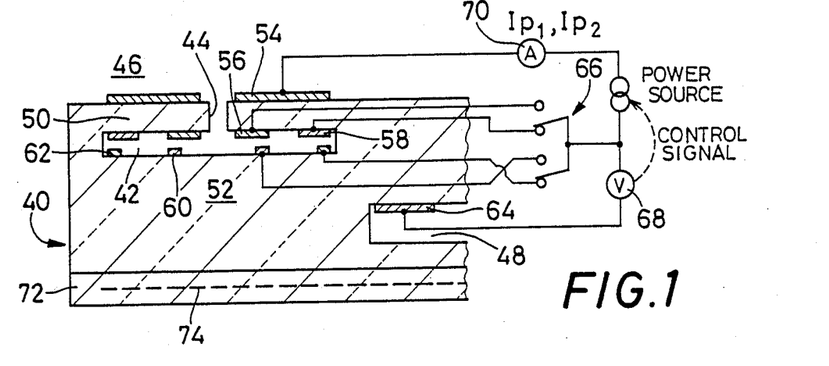
FIG. 1 is a fragmentary elevational view in cross section of a sensing element of one embodiment of an A/F-ratio sensor of the present invention, taken along line I—I of FIG. 6.
Figure 6:
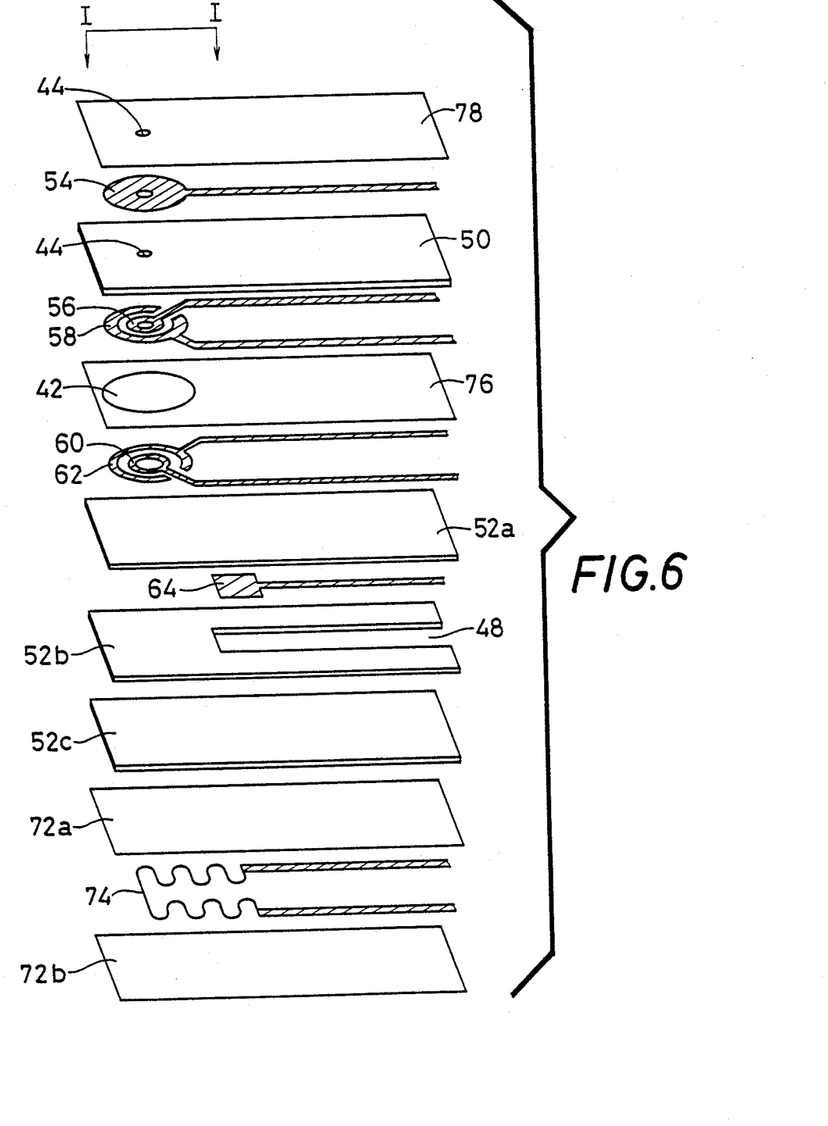
FIG. 6 is a perspective view of the sensing element of the A/F-ratio sensor of FIG. 1.

Referring first to the cross sectional view of FIG. 1, there is schematically shown in enlargement a detecting portion of the sensing element of the A/F-ratio sensor according to one embodiment of this invention. The sensing element has an integral laminar structure as depicted in FIG. 6.

In FIG. 1, reference numeral 40 designates a generally elongate planar solid electrolyte body which consists of a plurality of laminated layers of an oxygen-ion conductive solid electrolyte such as zirconia ceramics containing yttria. The laminated solid electrolyte layers are co-fired into the integral solid electrolyte body 40. In this solid electrolyte body 40, there is formed an internal gas-diffusion space in the form of a thin, circular flat space 42 which serves as diffusion-resistance means having a predetermined resistance to diffusion of a gas. This circular flat space 42 is formed parallel to the plane of the solid electrolyte body 40. In other words, the circular flat space 42 has a thickness or depth in a direction perpendicular to the opposite major surfaces of the solid electrolyte body 40. The central portion of the circular flat space 42 communicates through a gas-inlet aperture 44 with an external measurement-gas space 46 in which exhaust gases exists as a measurement gas. The solid electrolyte body 40 further has an air passage 48 formed therein parallel to its plane, so as to extend in the longitudinal direction.

The thickness of the circular flat space 42 is defined by an upper solid electrolyte layer 50 and a lower solid electrolyte layer 52, as seen in FIG. 1. On the outer surface of the upper solid electrolyte layer 50 of the body 40, there is disposed an annular outer pumping electrode 54 in aligned relation with the gas-inlet aperture 44, such that the inner periphery of the annular electrode 54 is radially outward of the aperture 44. On the inner suface of the upper solid electrolyte layer 50, there are disposed an annular first inner pumping electrode 56 and an annular second inner pumping electrode 58, such that these two annular inner pumping electrodes 56, 58 are concentric with the outer pumping electrode 54 and with each other. The first inner pumping electrode 56 is located radially outwardly of the aperture 44, and inwardly of the second inner pumping electrode 58. Namely, the first and second inner pumping electrodes 56, 58 are aligned with a radially inner and a radially outer portion of the circular flat space 42, respectively. Thus, two oxygen pumping cells (electrochemical cells) are provided. Described more specifically, the first oxygen pumping cell is constituted by the solid electrolyte layer 50, the outer pumping electrode 54 and the first inner pumping electrode 56, while the second oxygen pumping cell is constituted by the solid electrolyte layer 50, the outer pumping electrode 54 and the second inner pumping electrode 58.

On the surface of the lower solid electrolyte layer 52 which defines the flat space 42, there are disposed an annular first measuring electrode 60 and an annular second measuring electrode 62, such that these two measuring electrodes 60, 62 face the first and second inner pumping electrodes 56, 58, respectively, in concentric relation with these pumping electrodes 56, 58 and with each other. On the surface of the solid electrolyte layer 52 which defines the air passage 48, there is disposed a reference electrode 64 which cooperates with the first and second measuring electrodes 60, 62 to measure the oxygen concentrations of the atmospheres which surround the electrodes 60, 62. More specifically, a first oxygen sensing cell (electrochemical cell or oxygen concentration cell) is constituted by the lower solid electrolyte layer 52, the first measuring electrode 60 and the reference electrode 64. Further, a second oxygen sensing cell (electrochemical cell or oxygen concentration cell) is constituted by the solid electrolyte layer 52, the second measuring electrode 62 and the reference electrode 64.

The first oxygen pumping cell is operated to effect a pumping action based on an output of the first oxygen sensing cell which represents the oxygen concentration of the atmosphere in the first or radially inner portion of the circular flat space 42 adjacent to the central portion communicating with the aperture 44. The second oxygen pumping cell is operated to effect a pumping action based on an output of the second oxygen sensing cell which represents the oxygen concentration of the atmosphere in the second or radially outer portion of the circular flat space 42. A switch 66 is provided to selectively activate the first and second oxygen pumping cells based on the first and second oxygen sensing cells, in order to determine the A/F ratio of an air-fuel mixture which gives the exhaust gases in the external space 46. In FIG. 1, reference numeral 68 indicates a potentiometer which detects the output of the first and second sensing cells, namely, an electromotive force which is induced according to the principle of an oxygen concentration cell. Pump currents Ip1 and Ip2 applied to the first and second oxygen pumping cells are controlled based on the electromotive force detected by the potentiometer 68. Reference numeral 70 in FIG. 1 designates an ammeter adapted to detect the pump currents Ip1 and Ip2 which flow through the respective first and second pumping cells.

On the side of the solid electrolyte body 40 remote from the outer pumping electrode 54, there is provided a heater which includes a suitable electrically insulating ceramic layer 72 integrally formed with the solid electrolyte body 40, and a heat-generating element 74 embedded in the ceramic layer 72. The heat-generating element 74 is energized by an external power supply, to heat the oxygen pumping and sensing cells to suitable operating temperatures.

In the sensing element of the A/F-ratio sensor constructed as described above, the layers 50, 52 of the solid electrolyte body 40 may be made of suitable oxygen-ion conductive solid electrolyte materials other than preferably used zirconia ceramics indicated above, for example, $SrCeO_3$, and a solid solution of $Bi_2O_3$—$Y_2O_3$ and rare earth oxides. The electrodes 54, 56, 58, 60, 62, 64 are preferably porous layers which are formed of a mixture consisting of a metal of the platinum group such as platinum, palladium, rhodium, iridium, ruthenium or osmium, and a ceramic material such as zirconia, yttria or alumina. The mixture for the electrodes may be prepared by admixing a powder of the selected ceramic material to a powder of the selected platinum group metal, and the prepared powder mixture is applied in the appropriate shapes and fired in a well known manner.

When the oxygen concentration of the measurement gases or exhaust gases which represents the A/F ratio of the air-fuel mixture from which the exhaust gases are produced can be determined by the pump current Ip1 of the first oxygen pumping cell or Ip2 of the second oxygen pumping cell. Namely, the combination of the first pumping and sensing cells, or the combination of the second pumping and sensing cells is selected by operating the selector switch 66. During a long period of use of the A/F-ratio sensor, the diffusion resistance at the inlet of the thin flat space 42 may be varied due to a change in the geometric configuration or dimension of the gas diffusion path, for example, by a certain degree of clogging or plugging of the diffusion path. In this case, the pump currents Ip1' and Ip2' of the first and second pumping cells are obtained by operating the selector switch 66. Based on these measurements Ip1' and Ip2' of the used sensor, and the initial pump current values Ip1 and Ip2 of the sensor in the initial period of use, compensation values C, D for the first and second oxygen pumping cells are obtained to compensate the pump currents Ipl' and Ip2' for the amount of change in the diffusion resistance of the sensing element during use. Thus, the sensor can be re-calibrated so as to permit suitable compensation of the sensor output, and thereby assure accurate determination of the A/F ratio, even when the diffusion resistance of the sensing element is more or less changed during a long period of sevice.

The laminar structure of the sensing element of the A/F-ratio sensor shown in FIG. 1 is illustrated in detail in FIG. 6.

Referring to FIG. 6, the outer pumping electrode 54 is formed on one of opposite surfaces of the solid electrolye layer 50, while the first and second inner pumping electrodes 56, 58 are formed in concentric relation with each other on the other surface of the layer 50, whereby the two oxygen pumping cells are provided. The solid electrolyte layer 52 consists of three layers 52a, 52b and 52c. On the layer 52a which is nearest to the solid electrolyte layer 50, there are formed the first and second measuring electrodes 60, 62 such that these electrodes are radially aligned with the corresponding first and second inner pumping electrodes 56, 58. On the surface of the layer 52a remote from the measuring electrodes 60, 62, there is formed the reference electrode 64. Thus, the two oxygen sensing cells are provided. The solid electrolyte layer 52b, which is sandwiched between the layers 52a, 52c, has an elongate rectangular slot which cooperates with the upper and lower layers 52a and 52c to define the air passage 48, so that the reference electrode 64 is exposed to the passage 48 communicating with the ambient air.

Between the two pumping cells and the two sensing cells, that is, between the solid electrolyte layer 50 and the solid electrolyte layer 52a, there is interposed a spacer layer 76 which is formed of an electrically insulating ceramic material. This spacer layer 76 has a round aperture aligned with the electrodes 56, 58, 60, 62. With this spacer layer 76 sandwiched between the layers 50, 52a, there is defined the above-indicated thin, circular flat space 42 whose thickness is determined by the thickness of the spacer layer 76, so as to provide a predetermined diffusion resistance. As previously described, the two inner pumping electrodes 56, 58 of the two pumping cells, and the two measuring electrodes 60, 62 of the two sensing cells are exposed within the circular flat space 42.

The ceramic layer 72 of the heater formed on the outer side of the solid electrolyte layer 52c consists of an inner insulating layer 72a and an outer insulating layer 72b, between which the heat-generating element 74 is sandwiched. The outer pumping electrode 54, which is commonly used for the two pumping electrodes, is covered by a porous protective layer 78 formed of a ceramic material. The gas-inlet aperture 44 previously described is formed through the thicknesses of the protective layer 78, outer pumping electrode 54 and solid electrolyte layer 50, such that the aperture 44 communicates with the central portion of the circular flat space 42.

The laminar structure of the sensing element is prepared by superposing the appropriate green layers on each other, i.e., green layers for the pumping cell unit (50, 54, 56, 58, 78), spacer layer 76, sensing cell unit (52a, 52b, 52c, 60, 62, 64), and heater layer (72a, 74, 72b) The superposed green layers are fired into the integral structure.

Figure 7:
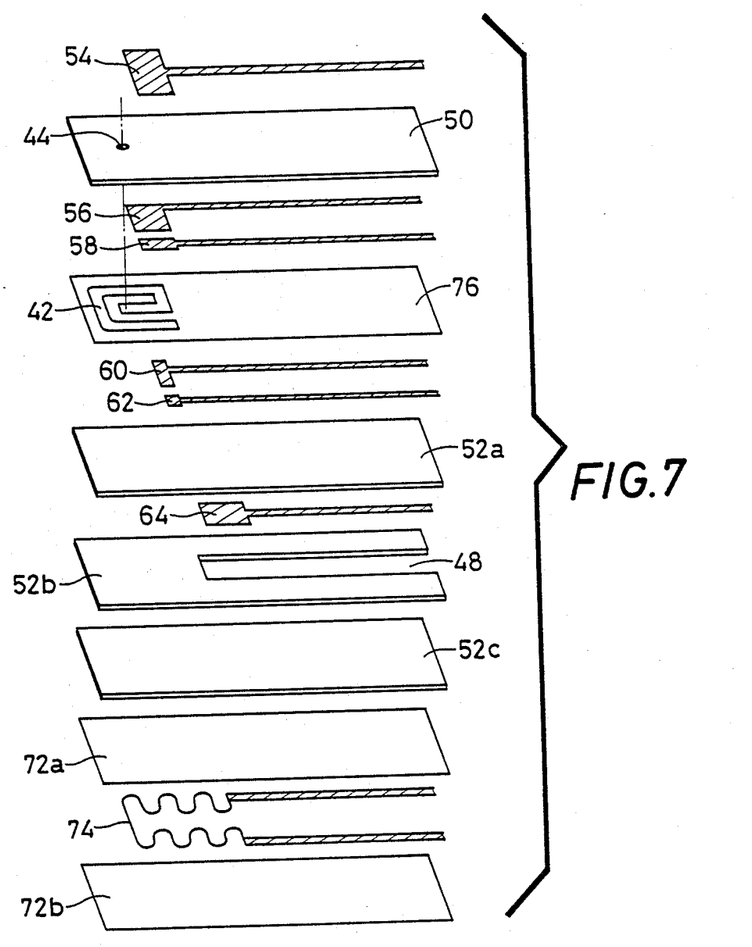
FIG. 7 is a perspective view of a sensing element of another embodiment of the A/F-ratio sensor of the invention.

Referring to FIG. 7, there is shown a sensing element of another embodiment of the A/F-ratio sensor of the present invention, which is characterized by a thin flat space 42 having a generally spiral or convoluted form as viewed perpendicularly to the plane of the sensing element.

In the sensing element of FIG. 7, the gas-inlet aperture 44 communicates with the central portion or inner end portion of the generally spiral thin flat space 42, so that the spiral space 42 communicates with the external measurement-gas space (as indicated at 46 in FIG. 1). The first inner pumping electrode 56 is located on the solid electrolyte layer 50, such that the electrode 56 is aligned with a portion of the spiral space 42 adjacent to the central or inner end portion. The second inner pumping electrode 58 is located on the layer 50, such that the electrode 58 is aligned with the outer end portion (second portion) of the spiral space 42. Further, the first measuring electrode 60 of the first sensing cell is positioned on the solid electrolyte layer 52a, in aligned relation with the first inner pumping electrode 56, i.e., aligned with the first or central portion of the spiral space 42, while the second measuring electrode 62 is aligned with the second inner pumping electrode 58, i.e., the second or outer end portion of the spiral space 42. The other parts of this sensing element are identical with the corresponding parts of the sensing element of FIGS. 1 and 6. The same reference numerals as used in FIGS. 1 and 6 are used in FIG. 7 to identify the corresponding parts.

In the sensing element of FIG. 7, the measurement exhaust gases introduced through the gas-inlet aperture 44 diffuse through the spiral path of the spiral flat space 42, under the predetermined diffusion resistance, so that the introduced exhaust gases first contact the first inner pumping electrode 56 and the first measuring electrode 60, and then contact the second inner pumping electrode 58 and the second measuring electrode 62 which are located at the outer end portion of the spiral space 42.

The thin flat space 42 formed as a gas-diffusion space within the sensing element may take various other forms than illustrated above, provided that the flat space 42 has a first portion into which the external measurement gas is introduced, and a second portion to which the introduced measurement gas diffuses under a predetermined diffusion resistance. For example, the flat space 42 may be a generally elongate straight space which has first and second portions that are spaced-apart from each other in the longitudinal direction.

The predetermined resistance of the flat space to the diffusion of the measurement gas between the first and second portions may be established by suitably determining the cross sectional area of the diffusion path or the diffusion length between the first and second portions.

FIGS. 8 through 13 show sensing elements having thin flat spaces 42, which are easily constructed so as to provide a desired diffusion resistance between the first and second portions, preferably so that the pump current of the first oxygen pumping cell is at least two times as large as that of the second oxygen pumping cell.

Figure 8:
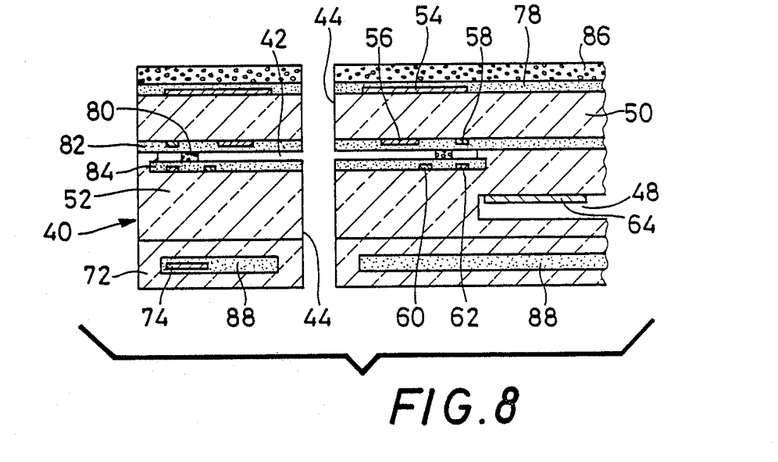
FIGS. 8 through 11 are cross sectional views corresponding to that of FIG. 1, showing sensing elements of further embodiments of the invention.

In the embodiment of FIG. 8, second diffusion-resistance means in the form of an annular porous body 80 made of alumina or similar material is disposed in the circular flat space 42, so as to fill an annular volume between the first portion aligned with the first inner pumping and measuring electrodes 56, 60, and the second portion aligned with the second inner pumping and measuring electrodes 58, 62. This porous body 80 has a higher diffusion resistance than the thin flat space 42, so that the diffusion of the measurement gas from the first portion to the second portion of the space 42 is restricted to the desired extent by the porous body 80.

Figure 9:
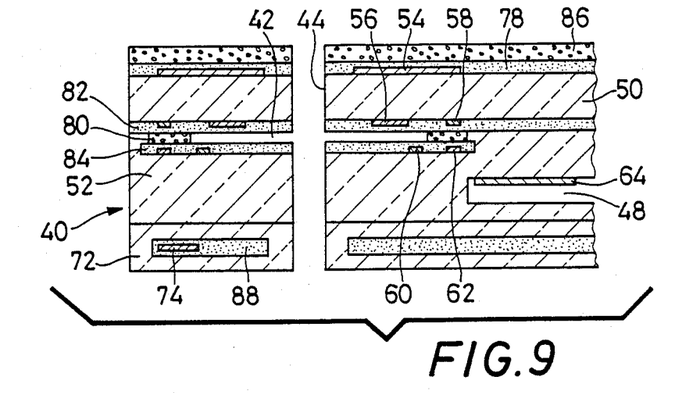

In the embodiment of FIG. 9, an annular porous body 80 similar to that used in the embodiment of FIG. 8 is disposed so as to fill a radially outer portion of the circular flat space 42 which includes the second portion but does not include the first portion. The measurement gas introduced into the first portion of the flat space 42 diffuses through the porous body 80 under a predetermined diffusion resistance, toward the second inner pumping electrode 58 and the second measuring electrode 62 which are located in the second portion of the space 42.

The above embodiments of FIGS. 8 and 9 are different from the embodiments of FIGS. 6 and 7, also in the following respects. That is, the gas-inlet aperture 44 is formed through the entire thickness of the sensing element. Further, the inner pumping electrodes 56, 58 and measuring electrodes 60, 62 which are exposed to the atmosphere within the flat space 42 are protected by respective first porous ceramic protective layers 82, 84. The common outer pumping electrode 54 is also protected by a second porous ceramic protective layer 86. Also, the heat-generating element 74 is embedded in a second electrically insulating layer 88 of alumina or similar material, which is embedded in the first electrically insulating layer, i.e., ceramic layer 72. Thus, the element 74 is protected by the two insulating layers 72, 88.

Figure 10:
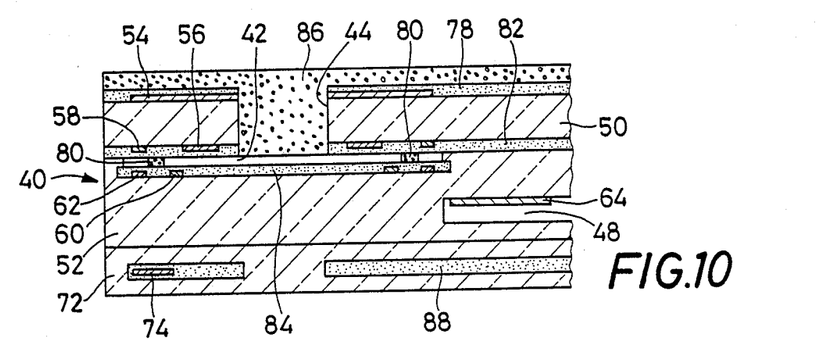

In the embodiment of FIG. 10, the second porous ceramic protective layer 86 has a protruding portion which fills the gas-inlet aperture 44 which communicates with the central portion of the circular flat space 42. This protruding portion of the porous protective layer 86 functions as a filter, which serves to trap particulate substances which would otherwise cause an undesirable clogging or plugging of the thin flat space 42 and adversely affect the output of the sensor. According to the instant arrangement, the diffusion of the measurement gas toward the first and second portions of the flat space 42 is restricted first by the porous body 86, and then by the small thickness of the flat space 42. In this sense, the present arrangement is considered to provide a theoretically ideal state of diffusion of the measurement gas toward the electrodes 56, 58, 60, 62.

Figure 11:
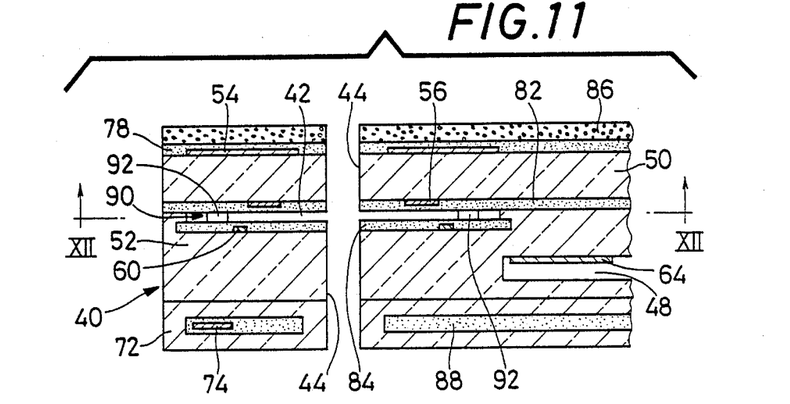
Figure 12:
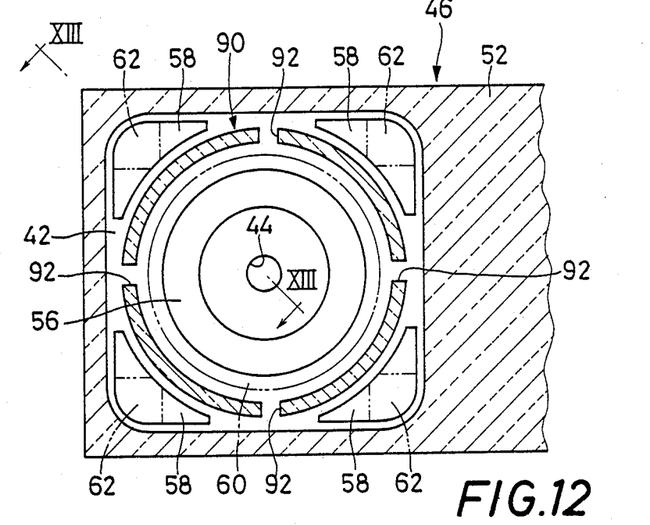
FIG. 12 is a view taken in a direction indicated by arrows XII—XII of FIG. 11.
Figure 13:
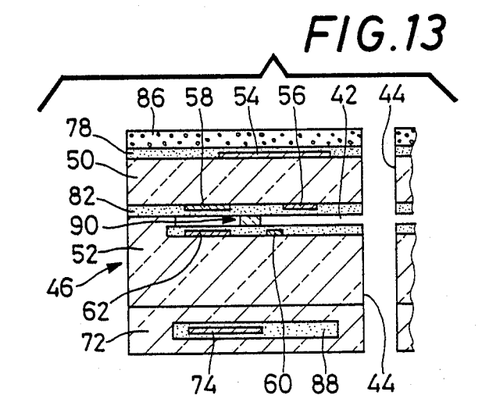
FIG. 13 is a cross sectional view taken along line XIII—XIII of FIG. 12.

The embodiment shown in FIGS. 11-13 is different from the embodiments of FIGS. 8, 9 and 10, in that the thin flat space 42 has a rectangular shape as viewed perpendicularly to the plane of the sensing element, as indicated in FIG. 12. The four corner portions of the rectangular flat space 42 serve as the second portion. In each of the four corner portions, the second inner pumping electrode 58 and the second measuring electrode 62 are disposed so as to face each other, as most clearly shown in FIG. 13. Adjacent to the central portion of the rectangular flat space 42 communicating with the gas-inlet aperture 44, there is disposed the first portion in which the annular first inner pumping electrode 56 and the annular first measuring electrode 60 are disposed. Radially outwardly of the first measuring electrode 60, there is formed partition means in the form of an annular partition 90 formed of a suitable ceramic material. The annular partition 90 has four cutouts 92 which are equally spaced apart from each other in the circumferential direction, at angular intervals of 90 degrees. The four cutouts 92 divide the partition 90 into four arcuate walls which are positioned so as to prevent radial straight or linear diffusion of the introduced measurement gas from the first portion of the flat space 42, toward the second portion (corner portions).

Described in more detail, the modified sensing element of FIGS. 11-13 is adapted such that the measurement gas introduced through the gas-inlet aperture 44 first contacts the first inner pumping electrode 56 and the first measuring electrode 60 which are disposed in the first portion of the rectangular flat space 42. Then, the introduced measurement gas diffuses from the first portion toward the second portion or corner portions, through the cutouts 92 formed in the annular partition 90, such that direct straight flows of the measurement gas from the central portion toward the corner portions of the rectangular space 42 are prevented by the four arcuate walls of the partition 90. Accordingly, the diffusion path from the first portion to the second portion of the space 42 is made comparatively long. Namely, the second inner pumping electrode 58 and the second measuring electrode 62 are exposed to the measurement gas which has diffused a distance considerably larger than the length of the otherwise possible linear diffusion between the first and second portions.

In the illustrated embodiments, the gas-inlet aperture 44 has a diameter which is so large that the diffusion resistance provided by the aperture 44 is substantially negligible. However, the aperture 44 may have a diameter small enough to provide a desired diffusion resistance, like a pin hole formed in a conventional sensor.

While the present invention has been described in its presently preferred embodiments with a certain degree of particularity, it is to be understood that the invention is not limited to the precise details of the illustrated embodiments, but the invention may be embodied with various changes, modifications and improvements which may occur to those skilled in the art, without departing from the spirit and scope of the invention defined in the following claims.

What is claimed is:

1. An oxygen sensor for detecting a measurement gas existing in an external space, which has a sensing element comprising:

means for defining a gas-diffusion space which communicates with said external space, said gas-diffusion space having a predetermined resistance to diffusion of the measurement gas therethrough, said gas-diffusion space including a first portion to which the measurement gas diffuses along a first diffusion path, and a second portion to which the measurement gas diffuses through said first portion along a second diffusion path which has a larger length than said first diffusion path;

first oxygen sensing means for producing a first output representative of an oxygen concentration of an atmosphere in said first portion of said gas-diffusion space;

first oxygen pumping means responsive to said first output from said first oxygen sensing means, for effecting an oxygen pumping action for controlling the oxygen concentration of said atmosphere in said first portion of said gas-diffusion space;

second oxygen sensing means for producing a second output representative of an oxygen concentration of an atmosphere in said second portion of said gas-diffusion space; and second oxygen pumping means responsive to said second output from said second oxygen sensing means, for effecting an oxygen pumping action for controlling the oxygen concentration of said atmosphere in said second portion of said gas-diffusion space.

2. An oxygen sensor according to claim 1, wherein said diffusion-gas space consists of a thin flat space which communicates with said external space.

3. An oxygen sensor according to claim 2, wherein said thin flat space communicates with said external space, through a gas-inlet aperture.

4. An oxygen sensor according to claim 3, wherein said thin flat space consists of a circular flat space having a thickness in a direction perpendicular to a major surface of said sensing element, said circular flat space having a central portion which communicates with said gas-inlet aperture, said first portion consisting of an annular portion disposed adjacent to and radially outwardly of said central portion, while said second portion consists of an annular portion disposed radially outwardly of said first portion.

5. An oxygen sensor according to claim 3, wherein said thin flat space consists of a generally spiral space having a thickness in a direction perpendicular to a major surface of said sensing element, said generally spiral space communicating at one of opposite end portions thereof with said gas-inlet aperture, said first portion being disposed adjacent to said one end portion, while said second portion consists of the other end portion.

6. An oxygen sensor according to claim 2, wherein said thin flat space consists of a generally elongate straight space, and said first and second portions are spaced apart from each other along a length of said straight space.

7. An oxygen sensor according to claim 3, wherein said sensing element further comprises a porous body which fills said gas-inlet aperture.

8. An oxygen sensor according to claim 1, wherein each of said first and second oxygen sensing means and said first and second oxygen pumping means consists of an electrochemical cell which comprises a solid electrolyte body, and a pair of electrodes.

9. An oxygen sensor according to claim 8, wherein said diffusion resistance of said gas-diffusion space is determined so that a first pump current which is applied to said first oxygen pumping means, so as to maintain the oxygen concentration of said atmosphere in said first portion at a predetermined value, is at least two times as large as a second pump current which is applied to said second oxygen pumping means, so as to maintain the oxygen concentration of said atmosphere in said second portion at said predetermined value.

10. An oxygen sensor according to claim 8, wherein one of said pair of electrodes of said first oxygen sensing means, and one of said pair of electrodes of said second oxygen sensing means are disposed in said first and second portions of said gas-diffusion space, respectively, the other electrode of said first oxygen sensing means and the other electrode of said second oxygen sensing means being constituted by a single common electrode which is disposed outside said gas-diffusion space.

11. An oxygen sensor according to claim 10, wherein said single common electrode is adapted to be exposed to a reference atmosphere which has a predeterminded oxygen partial pressure.

12. An oxygen sensor according to claim 8, wherein one of said pair of electrodes of said first oxygen pumping means, and one of said pair of electrodes of said second oxygen pumping means are disposed in said first and second portions of said gas-diffusion space, respectively, the other electrode of said first oxygen pumping means and the other electrode of said second oxygen pumping means being constituted by a single common electrode which is disposed outside said gas-diffusion space.

13. An oxygen sensor according to claim 8, wherein said solid electrolyte body is formed of an oxygen-ion conductive zirconia ceramic.

14. An oxygen sensor according to claim 8, wherein said sensing element further comprises a heater for maintaining said solid electrolyte body of each of said first and second oxygen sensing means and said first and second oxygen pumping means at a predetermined operating temperature.

15. An oxygen sensor according to claim 1, wherein said sensing element further comprises additional diffusion-resistance means which is disposed in a third portion of said gas-diffusion space between said first and second portions, said additional diffusion-resistance means having another predetermined resistance to diffusion of the measurement gas therethrough, which another predetermined resistance is greater than said predetermined resistance of said diffusion-resistance means.

16. An oxygen sensor according to claim 15, wherein said additional diffusion-resistance means consists of a porous body disposed in said third portion of said gas-diffusion space.

17. An oxygen sensor according to claim 16, wherein said gas-diffusion space communicates with said external space through a gas-inlet aperture, and said sensing element further comprises a second porous body which fills said gas-inlet aperture.

18. An oxygen sensor according to claim 1, wherein said sensing element further comprises additional diffusion-resistance means which is disposed in a third portion of said gas-diffusion space which includes said second portion, said additional diffusion-resistance means having another predetermined resistance to diffusion of the measurement gas therethrough, which another predetermined resistance is greater than said predetermined resistance of said diffusion-resistance means.

19. An oxygen sensor according to claim 18, wherein said additional diffusion-resistance means consists of a porous body disposed in said third portion of said gas-diffusion space.

20. An oxygen sensor according to claim 19, wherein said gas-diffusion space communicates with said external space through a gas-inlet aperture, and said sensing element further comprises a second porous body which fills said gas-inlet aperture.

21. An oxygen sensor according to claim 1, wherein said sensing element further comprises partition means disposed between said first and second portions of said gas-diffusion space, said partition means preventing a linear diffusion of said measurement gas from said first portion to said second portion, thereby providing a diffusion path which is longer than a length of said linear diffusion.

* * * * *